United States Patent [19]

Meier et al.

[11] Patent Number: 5,258,433
[45] Date of Patent: Nov. 2, 1993

[54] SULFOXIDES OF ALKYLTHIOMETHYLPHENOLS

[75] Inventors: Hans-Rudolf Meier; Paul Dubs, both of Marly, Switzerland

[73] Assignee: Ciba-Geigy Corporation, Ardsley, N.Y.

[21] Appl. No.: 747,569

[22] Filed: Aug. 20, 1991

[30] Foreign Application Priority Data

Aug. 28, 1990 [CH] Switzerland ............... 2788/90

[51] Int. Cl.⁵ ............... C08K 5/41; C07C 317/44; C07C 317/18
[52] U.S. Cl. ............... 524/155; 524/289; 560/9; 560/11; 560/15; 568/27
[58] Field of Search ............... 524/155, 289; 560/11, 560/9, 15; 568/27

[56] References Cited

U.S. PATENT DOCUMENTS

| | | | |
|---|---|---|---|
| 3,699,152 | 10/1972 | Hechenbleikner et al. | 560/15 |
| 3,810,869 | 5/1974 | Zaweski | 524/289 |
| 3,832,328 | 8/1974 | Eggensperger et al. | 524/289 |
| 4,021,468 | 5/1977 | Lind | 560/15 |
| 4,618,440 | 10/1986 | Steinberg et al. | 524/289 |
| 4,623,745 | 11/1986 | Rosenberger et al. | 560/15 |
| 4,759,862 | 7/1988 | Meier | 524/289 |
| 4,857,572 | 8/1989 | Meier et al. | 568/55 |

FOREIGN PATENT DOCUMENTS

| | | |
|---|---|---|
| 43-16741 | 7/1968 | Japan . |
| 49-27092 | 7/1974 | Japan . |
| 61-148287 | 7/1986 | Japan ............... 560/15 |
| 917370 | 2/1963 | United Kingdom . |
| 1396469 | 6/1975 | United Kingdom . |

OTHER PUBLICATIONS

Derwent Abst. No. 00,893Q (Japan 3773/68).

Primary Examiner—Veronica P. Hoke
Attorney, Agent, or Firm—Luther A. R. Hall; William A. Teoli, Jr.

[57] ABSTRACT

Sulfoxides of alkylthiomethylphenols of the formula I

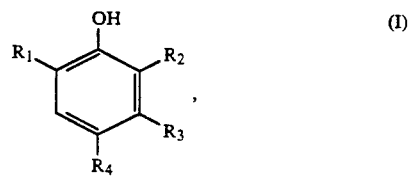

in which $R_1$ is hydrogen, $C_1$-$C_{20}$alkyl, $C_2$-$C_{18}$alkenyl, $C_5$-$C_7$cycloalkyl, $C_5$-$C_7$cycloalkenyl, phenyl or $C_7$-$C_9$-phenylalkyl, $R_2$ is hydrogen, $C_1$-$C_{20}$alkyl, $C_2$-$C_{18}$alkenyl, $C_5$-$C_7$cycloalkyl, $C_5$-$C_7$cycloalkenyl, phenyl, $C_7$-$C_9$phenylalkyl or a radical —$CH_2$—SO—$R_5$, in which $R_5$ is $C_8$-$C_{20}$alkyl which may be interrupted by —O—, —S— or —SO— groups, mono- or dihydroxy-substituted $C_2$-$C_{12}$alkyl, phenyl, benzyl, —$(CH_2)_n$COOR$_6$ or —CH(CH$_3$)COOR$_6$, in which $R_6$ is $C_1$-$C_{20}$alkyl and n is 1 or 2, $R_3$ is hydrogen or a group —CH$_2$—SO—$R_5$, in which $R_5$ is as defined above, and $R_4$ has the same meanings as $R_2$, with the proviso that only one of the radicals $R_2$, $R_3$ or $R_4$ is the group —CH$_2$—SO—$R_5$ and that, if $R_4$ is —CH$_2$—SO—$R_5$ and $R_1$ and $R_2$ are simultaneously tert-butyl or tert-amyl, $R_5$ is not $C_8$-$C_{14}$alkyl, or mixtures of these compounds with the corresponding non-oxidised compounds are suitable for stabilising organic materials which are sensitive to oxidative, thermal and/or light-induced degradation.

22 Claims, No Drawings

SULFOXIDES OF ALKYLTHIOMETHYLPHENOLS

The present invention relates to sulfoxides of alkylthiomethylphenols, mixtures of these sulfoxides with the non-oxidised compounds, compositions of organic materials comprising these compounds or mixtures, to the use of the abovementioned compounds and mixtures as stabilisers in organic materials which are sensitive to oxidative, thermal and/or light-induced degradation, and to a process for stabilising the abovementioned materials.

Alkylthiomethylated phenols and oxidation products thereof are used as stabilisers in organic polymers. See, for example, U.S. Pat. No. 4,759,862 and U.S. Pat. No. 4,857,572. (3,5-Disubstituted-4-hydroxybenzyl) sulfoxides are disclosed in JP-A-68/16741 as antioxidants in polyolefins. Compounds of this type are also used in polyolefin compositions in JP-A-74/27092. In JP-A-68/3773 analogous compounds dioxidised on the sulfur atom are described. GB-A-917,370 discloses bis(3,5-disubstituted-4-hydroxybenzyl) sulfoxides as antioxidants for organic materials. Furthermore, GB-A-1,396,469 describes other alkylthioalkylenephenols oxidised on the S atom as stabilisers.

In the area of antioxidants for organic polymers, there is still a demand for active compounds. In particular in the area of elastomers and lubricants, new application technologies and new compositions require adjustments with respect to stabilisation of the substrate. It has now been found that certain sulfoxides of alkylthiomethylphenols are highly suitable for stabilising organic materials which are sensitive to oxidative, thermal and/or light-induced degradation.

The present invention relates to compounds of the formula I

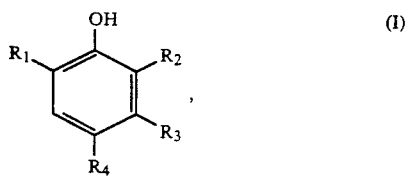

in which $R_1$ is hydrogen, $C_1$-$C_{20}$alkyl, $C_2$-$C_{18}$alkenyl, $C_5$-$C_7$cycloalkyl, $C_5$-$C_7$cycloalkenyl, phenyl or $C_7$-$C_9$phenylalkyl, $R_2$ is hydrogen, $C_1$-$C_{20}$alkyl, $C_2$-$C_{18}$alkenyl, $C_5$-$C_7$cycloalkyl, $C_5$-$C_7$cycloalkenyl, phenyl, $C_7$-$C_9$phenylalkyl or a radical —$CH_2$—SO—$R_5$, in which $R_5$ is $C_8$-$C_{20}$alkyl which may be interrupted by —O—, —S— or —SO— groups, mono- or dihydroxy-substituted $C_2$-$C_{12}$alkyl, phenyl, benzyl, —($CH_2$)$_n$COOR$_6$ or —CH($CH_3$)COOR$_6$, in which $R_6$ is $C_1$-$C_{20}$alkyl and n is 1 or 2, $R_3$ is hydrogen or a group —$CH_2$—SO—$R_5$, in which $R_5$ is as defined above, and $R_4$ has the same meaning as $R_2$, with the proviso that only one of the radicals $R_2$, $R_3$ or $R_4$ is the group —$CH_2$—SO—$R_5$ and that, if $R_4$ is —$CH_2$—SO—$R_5$ and $R_1$ and $R_2$ are simultaneously tert-butyl or tert-amyl, $R_5$ is not $C_8$-$C_{14}$alkyl.

$R_1$, $R_2$, $R_4$ and $R_6$ as $C_1$-$C_{20}$alkyl can be linear or branched and be, for example, methyl, ethyl, n-propyl, isopropyl, n-butyl, tert-butyl, n-pentyl, isopentyl, n-hexyl, 2-ethylhexyl, n-heptyl, n-octyl, i-octyl, tert-octyl, decyl, dodecyl, tetradecyl, octadecyl or eicosyl. $R_1$ and $R_2$ as alkyl are preferably $C_1$-$C_{18}$alkyl, particularly preferably $C_1$-$C_{12}$alkyl, and in particular $C_1$-$C_9$alkyl. $R_4$ as alkyl is preferably $C_1$-$C_{18}$alkyl. $R_6$ as alkyl is preferably $C_8$-$C_{18}$alkyl, in particular $C_{13}$alkyl.

$R_5$ as $C_8$-$C_{20}$alkyl can be linear or branched and have the same meanings as mentioned for $R_1$, $R_2$, $R_4$ and $R_6$, starting with the corresponding number of C atoms. Preferred alkyl groups $R_5$ are $C_8$-$C_{12}$alkyl.

$R_1$, $R_2$ and $R_4$ as $C_2$-$C_{18}$alkenyl can be, for example, vinyl, allyl, methallyl, 1,1-dimethylallyl, butenyl, hexenyl, octenyl, undecenyl, dodecenyl or octadecenyl.

$R_5$ as mono- or dihydroxy-substituted $C_2$-$C_{12}$alkyl can be a linear or branched substituted alkyl and be, for example, 2-hydroxyethyl, 1,2-dihydroxyethyl, hydroxy- or dihydroxypropyl, -butyl, -pentyl, -hexyl, -heptyl, -octyl, -nonyl, -decyl, -undecyl, -dodecyl, in particular 2-hydroxyethyl or 2,3-dihydroxypropyl.

$R_1$, $R_2$ and $R_4$ as $C_5$-$C_7$cycloalkyl can be cyclopentyl, cyclohexyl and cycloheptyl, in particular cyclopentyl or cyclohexyl.

Examples of $R_1$, $R_2$ and $R_4$ as $C_5$-$C_7$cycloalkenyl are cyclopentenyl, cyclohexenyl and cycloheptenyl, in particular cyclopentenyl or cyclohexenyl.

Examples of $R_1$, $R_2$ and $R_4$ as $C_7$-$C_9$phenylalkyl are benzyl, phenylethyl, α-methylbenzyl, 3-phenylpropyl, 2-methylphenylethyl, 1-methylphenylethyl or α,α-dimethylbenzyl, in particular benzyl.

Compounds of the formula I in which $R_1$ is hydrogen, $C_1$-$C_{18}$alkyl, $C_5$-$C_6$cycloalkyl or $C_5$-$C_7$cycloalkenyl, $R_2$ has the same definition as $R_1$ or is —$CH_2$—SO—$R_5$, $R_3$ is hydrogen, $R_4$ is hydrogen, $C_1$-$C_{18}$alkyl or —$CH_2$—SO—$R_5$, $R_5$ is $C_8$-$C_{20}$alkyl, phenyl, benzyl or —$CH_2$COOR$_6$ and $R_6$ is $C_1$-$C_{20}$alkyl are of particular interest.

Furthermore, preference is given to compounds of the formula I in which $R_1$ is hydrogen, $C_1$-$C_{18}$alkyl, in particular $C_1$-$C_{12}$alkyl, cyclopentenyl or cyclohexenyl, $R_2$ is hydrogen, $C_1$-$C_{18}$alkyl, in particular $C_1$-$C_{12}$alkyl, especially $C_1$-$C_4$alkyl, cyclopentenyl, cyclohexenyl or —$CH_2$—SO—$R_5$, $R_3$ is hydrogen, $R_4$ is hydrogen, $C_1$-$C_{18}$alkyl, in particular $C_1$-$C_{12}$alkyl or —$CH_2$—SO—$R_5$, $R_5$ is $C_8$-$C_{20}$alkyl, phenyl, benzyl or —$CH_2$COOR$_6$ and $R_6$ is $C_6$-$C_{20}$alkyl.

Other preferred compounds of the formula I are those in which $R_1$ is $C_1$-$C_{18}$alkyl, $R_2$ is $C_1$-$C_{12}$alkyl, cyclopentenyl or —$CH_2$—SO—$R_5$, $R_3$ is hydrogen, $R_4$ is $C_1$-$C_{12}$alkyl or —$CH_2$—SO—$R_5$, $R_5$ is $C_8$-$C_{20}$alkyl, phenyl, benzyl, —$CH(CH_3)$COOR$_6$, —$CH_2CH_2$OH or —$CH_2$COOR$_6$ and $R_6$ is $C_6$-$C_{20}$alkyl.

Preference is given to compounds of the formula I in which $R_1$ is hydrogen, $C_1$-$C_{18}$alkyl, $C_5$-$C_6$cycloalkyl or $C_5$-$C_6$cycloalkenyl, $R_2$ is —$CH_2$—SO—$R_5$, $R_3$ is hydrogen, $R_4$ is $C_1$-$C_{18}$alkyl, $C_5$-$C_6$cycloalkyl or $C_5$-$C_6$cycloalkenyl and $R_5$ is $C_8$-$C_{20}$alkyl, phenyl, benzyl or —$CH_2$COOR$_6$.

Furthermore, preference is given to compounds of the formula I in which $R_1$ is hydrogen, $C_1$-$C_{12}$alkyl or $C_5$-$C_6$cycloalkyl and $R_5$ is $C_8$-$C_{18}$alkyl, phenyl, benzyl or —$CH_2$COOR$_6$.

Compounds of the formula I in which $R_1$ is $C_1$-$C_9$alkyl and $R_5$ is $C_8$-$C_{12}$alkyl, phenyl or benzyl, in particular compounds in which $R_5$ is $C_8$-$C_{12}$alkyl, are also of particular interest.

Furthermore, compounds of the formula I in which $R_1$ and $R_2$, independently of one another, are $C_1$-$C_{18}$alkyl, $C_5$-$C_6$cycloalkyl or $C_5$-$C_6$cycloalkenyl, $R_3$ is hydrogen and $R_4$ is a radical —$CH_2$—SO—$R_5$, in which $R_5$ is $C_8$-$C_{18}$alkyl, phenyl, benzyl, —$CH_2CH_2$OH or —($CH_2$)$_n$COOR$_6$, are preferred.

Compounds of the formula I in which $R_4$ is a radical —$CH_2$—SO—$R_5$ and $R_5$ is —$(CH_2)_n COOR_6$ are also of particular interest.

Preference is also given to compounds of the formula I in which $R_1$ and $R_2$, independently of one another, are $C_1$–$C_{12}$alkyl, $C_5$–$C_6$cycloalkyl or $C_5$–$C_6$cycloalkenyl and $R_5$ is $C_8$–$C_{18}$alkyl, phenyl, benzyl or —$(CH_2)_n COOR_6$.

Particular preference is given to compounds of the formula I in which $R_1$ is $C_1$–$C_9$alkyl and $R_5$ is $C_8$–$C_{12}$alkyl, phenyl or benzyl, in particular those compounds in which $R_5$ is $C_8$–$C_{12}$alkyl.

Compounds of the formula I in which $R_2$ is —$CH_2$—SO—$R_5$ are particularly advantageous.

Furthermore, compounds of the formula I in which, if $R_4$ is —$CH_2$—SO—$R_5$ and $R_1$ and $R_2$ are simultaneously tert-butyl, tert-amyl or isopropyl, $R_5$ is not $C_8$–$C_{14}$alkyl, preferably not $C_8$–$C_{14}$alkyl or phenyl, may be mentioned in particular.

The invention also relates to compounds of the formula II

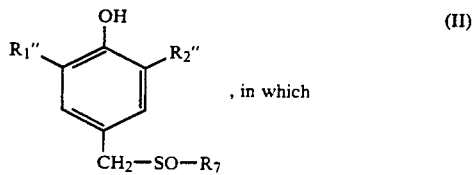

, in which $R_1''$ and $R_2''$ are tert-butyl or tert-amyl and $R_7$ is branched $C_8$–$C_{14}$alkyl or isomeric mixtures of a $C_8$–$C_{14}$alkyl.

Preference is given to compounds of the formula II in which $R_7$ is tert-nonyl, tert-dodecyl or sec-octyl.

The invention also relates to mixtures of compounds of the formula I or II with compounds of the formula III

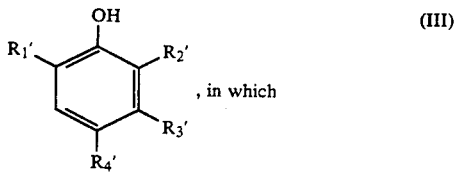

, in which $R_1'$ is hydrogen, $C_1$–$C_{20}$alkyl, $C_2$–$C_{18}$alkenyl, $C_5$–$C_7$cycloalkyl, $C_5$–$C_7$cycloalkenyl, phenyl or $C_7$–$C_9$phenylalkyl, $R_2'$ is hydrogen, $C_1$–$C_{20}$alkyl, $C_2$–$C_{18}$alkenyl, $C_5$–$C_7$cycloalkyl, $C_5$–$C_7$cycloalkenyl, phenyl, $C_7$–$C_9$phenylalkyl or a radical —$CH_2$—S—$R_5$, in which $R_5$ is $C_8$–$C_{20}$alkyl which may be interrupted by —O—, —S— or —SO— groups, mono- or dihydroxy-substituted $C_2$–$C_{12}$alkyl, phenyl, benzyl, —$(CH_2)_n COOR_6$ or —$CH(CH_3)COOR_6$, in which $R_6$ is $C_1$–$C_{20}$alkyl and n is 1 or 2, $R_3'$ is hydrogen or a group —$CH_2$—S—$R_5$, in which $R_5$ is as defined above, and $R_4'$ has the same meanings as $R_2'$, with the proviso that only one of the radicals $R_2'$, $R_3'$ or $R_4'$ is the group —$CH_2$—S—$R_5$.

Preferred mixtures are those in which the compounds of the formula I or II differ from those of formula III only by the latter containing —S— groups instead of —SO— groups but otherwise have the same structure as the former.

Mixtures obtainable by partial oxidation of at least one compound of the formula III are of interest.

Mixtures in which the ratio of the compounds of the formula III to those of the formula I or II is 1:9 to 9:1, in particular 1:9 to 1:1, are of particular interest.

The invention also relates to compositions comprising an organic material which is sensitive to oxidative, thermal and/or light-induced degradation and at least one compound of the formula I or II or at least one mixture of compounds of the formula I or II with compounds of the formula III, and to the use of the compounds and mixtures mentioned for stabilising organic materials which are sensitive to oxidative, thermal and/or light-induced degradation. Preference is given to compositions comprising at least one compound of the formula I or II and an organic material which is sensitive to oxidative, thermal and/or light-induced degradation.

Examples of organic materials of this type which may be mentioned and which are present in the compositions according to the invention and can be stabilised according to the invention are:

1. Polymers of monoolefins and diolefins, for example polypropylene, polyisobutylene, polybut-1-ene, polymethylpent-1-ene, polyisoprene or polybutadiene, as well as polymers of cycloolefins, for example of cyclopentene or norbornene; as well as polyethylene (which if desired can be crosslinked), for example high-density polyethylene (HDPE), low-density polyethylene (LDPE), linear low-density polyethylene (LLDPE) and branched low-density polyethylene (BLDPE).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, such as, for example, ethylene/propylene copolymers, linear low-density polyethylene (LLDPE) and its mixtures with low-density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and copolymers thereof with carbon monoxide, or ethylene/acrylic acid copolymers and their salts (ionomers) and terpolymers of ethylene with propylene and a diene, such as hexadiene, dicyclopentadiene or ethylidenenorbornene; as well as mixtures of such copolymers with each other and with polymers mentioned in 1), for example polypropylene/ethylene-propylene copolymers, LDPE/ethylene-vinyl acetate copolymers, LDPE/ethylene-acrylic acid copolymers, LLDPE/ethylene-vinyl acetate copolymers and LLDPE/ethylene-acrylic acid copolymers, polyalkylene/carbon monoxide copolymers of alternating or random structure and mixtures thereof with other polymers, for example polyamides.

3a. Hydrocarbon resins (for example $C_5$–$C_9$), including hydrogenated modifications thereof (for example tackifying resins) and mixtures of polyalkylenes and starch.

4. Polystyrene, poly-(p-methylstyrene), poly-(α-methylstyrene).

5. Copolymers of styrene or α-methylstyrene with dienes or acrylic derivatives, for example styrene/butadiene, styrene/acrylonitrile, styrene/alkyl methacrylate, styrene/butadiene/alkyl acrylate and methacrylate, styrene/maleic anhydride, styrene/acrylonitrile/methyl acrylate; mixtures of high impact strength from copolymers of styrene and another polymer, for example a polyacrylate, a diene polymer or an ethylene/propylene/diene terpolymer; and block copolymers of styrene, for example styrene/butadiene/styrene, styrene/isoprene/styrene, styrene/ethylene-butylene/styrene or styrene/ethylene-propylene/styrene.

6. Graft copolymers of styrene or α-methylstyrene, for example styrene on polybutadiene, styrene on copolymers of polybutadiene-styrene or polybutadiene-acrylonitrile; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or alkyl methacrylates on polybutadiene; styrene and acrylonitrile on ethylene/propylene/diene terpolymers; styrene and acrylonitrile on polyalkylacrylates or polyalkylmethacrylates; styrene and acrylonitrile on acrylate/butadiene copolymers, as well as mixtures thereof with the copolymers listed under 5), for example those known as so-called ABS, MBS, ASA and AES polymers.

7. Halogen-containing polymers, such as polychloroprene, chlorinated rubber, chlorinated or sulfochlorinated polyethylene, copolymers of ethylene and chlorinated ethylene, epichlorohydrin homo- and copolymers, in particular polymers from halogen-containing vinyl compounds, for example polyvinyl chloride, polyvinylidene chloride, polyvinyl fluoride, polyvinylidene fluoride, as well as copolymers thereof, such as vinyl chloride/vinylidene chloride, vinyl chloride/vinyl acetate or vinylidene chloride/vinyl acetate.

8. Polymers which are derived from α,β-unsaturated acids and derivatives thereof, such as polyacrylates and polymethacrylates, polymethyl methacrylates, polyacrylamides and polyacrylonitriles made impact-resistant by modification with butyl acrylate.

9. Copolymers of the monomers mentioned under 8) with each other or with other unsaturated monomers, for example acrylonitrile/butadiene copolymers, acrylonitrile/alkyl acrylate copolymers, acrylonitrile/alkoxyalkyl acrylate copolymers, acrylonitrile/vinyl halide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinyl butyral, polyallyl phthalate or polyallylmelamine; as well as their copolymers with olefins mentioned in 1).

11. Homopolymers and copolymers of cyclic ethers, such as polyalkylene glycols, polyethylene oxide, polypropylene oxide or copolymers thereof with bis(glycidyl) ethers.

12. Polyacetals, such as polyoxymethylene and polyoxymethylenes which contain comonomers, ethylene oxide for example; polyacetals modified with thermoplastic polyurethanes, acrylates or MBS.

13. Polyphenylene oxides and sulfides, and mixtures thereof with styrene polymers or polyamides.

14. Polyurethanes which are derived from polyethers, polyesters and polybutadienes with terminal hydroxyl groups on the one hand and aliphatic or aromatic polyisocyanates on the other hand, as well as precursors thereof.

15. Polyamides and copolyamides which are derived from diamines and dicarboxylic acids and/or from aminocarboxylic acids or the corresponding lactams, such as nylon 4, nylon 6, nylon 6/6, 6/10, 6/9, 6/12, 4/6 and 12/12, nylon 11, nylon 12, aromatic polyamides obtained starting from m-xylene, diamine and adipic acid; polyamides prepared from hexamethylenediamine and isophthalic and/or terephthalic acid and, if desired, an elastomer as modifier, for example poly-2,4,4-trimethyl-hexamethylene terephthalamide or poly-m-phenylene-isophthalamide. Block copolymers of the aforementioned polyamides with polyolefins, olefin copolymers, ionomers or chemically bounded or grafted elastomers; or with polyethers, for example with polyethylene glycol, polypropylene glycol or polytetramethylene glycol. In addition, polyamides or copolyamides modified with EPDM or ABS; as well as polyamides condensed during processing (RIM-polyamide systems).

16. Polyureas, polyimides, polyamide-imides and polybenzimidazoles.

17. Polyesters which are derived from dicarboxylic acids and dialcohols and/or from hydroxycarboxylic acids or the corresponding lactones, such as polyethylene terephthalate, polybutylene terephthalate, poly-1,4-dimethylolcyclohexane terephthalate, polyhydroxybenzoates, as well as block polyether esters derived from polyethers having hydroxyl end groups; in addition polyesters modified with polycarbonates or MBS.

18. Polycarbonates and polyester carbonates.

19. Polysulfones, polyether sulfones and polyether ketones.

20. Crosslinked polymers which are derived from aldehydes on the one hand and phenols, urea or melamine on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Crosslinkable acrylic resins, derived from substituted acrylic esters, for example epoxy acrylates, urethane acrylates or polyester acrylates.

24. Alkyd resins, polyester resins or acrylate resins which are crosslinked with melamine resins, urea resins, polyisocyanates or epoxy resins.

25. Crosslinked epoxy resins which are derived from polyepoxides, for example from bis(glycidyl) ethers or from cycloaliphatic diepoxides.

26. Natural polymers, such as cellulose, rubber, gelatin and derivatives thereof which are chemically modified in a polymer-homologous manner, such as cellulose acetates, cellulose propionates and cellulose butyrates, or cellulose ethers, such as methylcellulose; and rosin resins and their derivatives.

27. Mixtures (polyblends) of the polymers mentioned above, for example PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/nylon and copolymers, PA/HDPE, PA/PP, PA/PPO.

28. Naturally occurring and synthetic organic materials which are pure monomeric compounds or mixtures of such compounds, for example mineral oils, animal and vegetable fats, oils and waxes, or oils, waxes and fats based on synthetic esters (e.g. phthalates, adipates, phosphates or trimellitates) and also mixtures of synthetic esters with mineral oils in any weight ratio, which mixtures may be used as spinning preparations, as well as aqueous emulsions thereof.

29. Aqueous emulsions of natural or synthetic rubbers, for example natural latex or latices of carboxylated styrene/butadiene copolymers.

The compositions advantageously contain 0.01–10% by weight of the compounds or mixtures according to the invention, relative to the organic material, in particular 0.05–5.0% by weight, preferably 0.05–3% by weight, for example 0.1–2% by weight.

The material which is sensitive to oxidative, thermal and/or light-induced degradation can be, for example, an organic polymer, a lubricant or a hydraulic fluid. The organic polymers are preferably synthetic polymers, in particular elastomers.

Particular preference is given to compositions comprising elastomers or lubricants and at least one compound of the formula I or II or mixtures of at least one compound of the formula I or II with at least one compound of the formula III and to the use of these compounds and mixtures as stabilisers for the materials mentioned.

The invention also relates to a process for stabilising organic materials which are sensitive to oxidative, thermal and/or light-induced degradation, which comprises incorporating a compound of the formula I or II or mixtures of at least one compound of the formula I or II with at least one compound of the formula III into these materials or applying them thereto.

Suitable lubricants are based, for example, on mineral or synthetic oils or mixtures thereof. The lubricants are familiar to the person skilled in the art and are described in the relevant specialist literature, for example in Dieter Klamann, "Schmierstoffe und verwandte Produkte" [Lubricants and Related Products] (Verlag Chemie, Weinheim, 1982), in Schewe-Kobek, "Das Schmiermittel-Taschenbuch" [The Lubricant Handbook] (Dr. Alfred Hüthig-Verlag, Heidelberg, 1974) and in "Ullmanns Enzyklopädie der technischen Chemie" [Ullmann's Encyclopaedia of Industrial Chemistry], vol. 13, pages 85–94 (Verlag Chemie, Weinheim, 1977).

The lubricants are in particular oils and fats, for example based on a mineral oil. Oils are preferred.

A further group of lubricants which can be used are vegetable or animal oils, fats, tallows and waxes or mixtures thereof with each other or mixtures with the mineral or synthetic oils mentioned. Vegetable and animal oils, fats, tallows and waxes are, for example, palm kernel oil, palm oil, olive oil, rapeseed oil or rape oil, linseed oil, groundnut oil, soya bean oil, cotton oil, sunflower oil, pumpkin seed oil, coconut oil, maize oil, castor oil, walnut oil and mixtures thereof, fish oils, tallow from slaughtered animals such as bovine tallow, neatsfoot oil and bone oil and their modified, epoxidised and sulfoxidised forms, for example epoxidised soya bean oil.

The mineral oils are based in particular on hydrocarbon compounds.

Examples of synthetic lubricants include lubricants based on aliphatic or aromatic carboxylic esters, the polymeric esters, the polyalkylene oxides, the phosphoric acid esters, the poly-α-olefins or the silicones, on a diester of a dibasic acid with a monohydric alcohol, for example dioctyl sebacate or dinonyl adipate, on a triester of trimethylolpropane with a monobasic acid or with a mixture of such acids, for example trimethylolpropane tripelargonate, trimethylolpropane tricaprylate or mixtures thereof, on a tetraester of pentaerythritol with a monobasic acid or with a mixture of such acids, for example pentaerythritol tetracaprylate, or on a complex ester of monobasic and dibasic acids with polyhydric alcohols, for example a complex ester of trimethylolpropane with caprylic and sebacic acid or of a mixture thereof. Particularly suitable in addition to mineral oils are, for example, poly-α-olefins, lubricants based on esters, phosphates, glycols, polyglycols and polyalkylene glycols, and mixtures thereof with water.

The compositions according to the invention can, for example, contain the following materials as elastomers:

1. Polydienes, for example polybutadiene, polyisoprene or polychloroprene; block polymers, for example styrene/butadiene/styrene, styrene/isoprene/styrene or acrylonitrile/butadiene copolymers.

2. Copolymers of mono- and diolefins with one another or with other vinyl monomers, for example ethylene/alkyl acrylate copolymers, ethylene/alkyl methacrylate copolymers, ethylene/vinyl acetate copolymers and terpolymers of ethylene with propylene and a diene, such as hexadiene, dicyclopentadiene or ethylidenenorbornene.

3. Halogen-containing polymers, for example polychloroprene, chlorinated rubber, chlorinated or chlorosulfonated polyethylene, epichlorohydrin homo- and copolymers, chlorotrifluoroethylene copolymers, polymers composed of halogen-containing vinyl compounds, for example polyvinylidene chloride, polyvinylidene fluoride; and copolymers thereof, such as vinyl chloride/vinylidene chloride, vinyl chloride/vinyl acetate or vinylidene chloride/vinyl acetate.

4. Polyurethanes derived on the one hand from polyethers, polyesters and polybutadiene having terminal hydroxyl groups and, on the other hand, from aliphatic or aromatic polyisocyanates and their precursors.

5. Natural rubber.

6. Mixtures (polyblends) of the abovementioned polymers.

7. Aqueous emulsions of natural or synthetic rubbers, for example natural rubber latex or latices of carboxylated styrene/butadiene copolymers.

If desired, these elastomers are present as latices and can be stabilised as such.

Preference is given to compositions containing a polydiene, such as polybutadiene rubber, a halogen-containing polymer, such as polyvinylidene fluoride, or a polyurethane as the elastomer.

Incorporation into the organic materials can be carried out, for example, by mixing in the compounds or mixtures according to the invention and, if desired, other additives by the methods customary in industry. If they are polymers, in particular synthetic polymers, incorporation can be carried out before or during moulding, or by applying the dissolved or dispersed compounds to the polymers, if appropriate with subsequent evaporation of the solvent. In the case of elastomers, these can also be stabilised as latices. A further possibility for incorporation of the compounds or mixtures according to the invention into polymers comprises their addition before or during polymerisation of the corresponding monomers or before crosslinking. In the case of addition before or during polymerisation, the compounds of the formula I or II or the mixtures according to the invention of compounds of the formula I or II with compounds of the formula III can also act as regulators for the chain length of the polymers (chain terminators).

The compounds or mixtures according to the invention can also be added to the plastics to be stabilised in the form of a masterbatch which contains these compounds, for example, in a concentration of 2.5 to 25% by weight.

Polymer compositions according to the invention can be used in various forms or processed to give various products, for example as (to give) foils, fibres, tapes, moulded materials, profiles or as binders for paints, adhesives or cement.

Lubricant compositions according to the invention are used, for example, in internal combustion engines, for example in motor vehicles.

In addition to the compounds or mixtures according to the invention, the compositions according to the invention can contain still other customary additives, in particular if they contain organic, preferably synthetic polymers. Examples of such additives are:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-dinonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-didodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl)adipate.

1.4. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl) disulfide.

1.5. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methylphenyl)-dicyclopentadiene, bis[2-(3'-tert-butyl-2'-hydroxy-5'-methylbenzyl)-6-tert-butyl-4-methylphenyl]terephthalate, 1,1-bis(3,5-dimethyl-2-hydroxyphenyl)butane, 2,2-bis(3,5-di-tert-butyl-4-hydroxyphenyl)propane, 2,2-bis(5-tert-butyl-4-hydroxy-2-methylphenyl)-4-n-dodecylmercaptobutane, 1,1,5,5-tetra(5-tert-butyl-4-hydroxy-2-methylphenyl)pentane.

1.6. O-, N- and S-Benzyl compounds, for example 3,5,3',5'-tetra-tert-butyl-4,4'-dihydroxydibenzyl ether, octadecyl-4-hydroxy-3,5-dimethylbenzyl mercaptoacetate, tris(3,5-di-tert-butyl-4-hydroxybenzyl)amine, bis(4-tert-butyl-3-hydroxy-2,6-dimethylbenzyl) dithioterephthalate, bis(3,5-di-tert-butyl-4-hydroxybenzyl) sulfide, isooctyl 3,5-di-tert-butyl-4-hydroxybenzyl-mercaptoacetate.

1.7. Hydroxybenzylated malonates, for example dioctadecyl 2,2-bis(3,5-di-tert-butyl-2-hydroxybenzyl)malonate, dioctadecyl-2-(3-tert-butyl-4-hydroxy-5-methylbenzyl)malonate, didodecylmercaptoethyl 2,2-bis(3,5-di-tert-butyl-4-hydroxybenzyl)malonate, di[4-(1,1,3,3-tetramethylbutyl)phenyl]2,2-bis(3,5-di-tert-butyl-4-hydroxybenzyl)malonate.

1.8. Hydroxybenzyl aromatics, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.9. Triazine compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,3,5-triazine, 1,3,5-tris(3,5-di-tert-butyl-4-hydroxybenzyl) isocyanurate, 1,3,5-tris(4-tert-butyl-3-hydroxy-2,6-dimethylbenzyl) isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)hexahydro-1,3,5-triazine, 1,3,5-tris(3,5-dicyclohexyl-4-hydroxybenzyl)isocyanurate.

1.10. Benzyl phosphonates, for example dimethyl-2,5-di-tert-butyl-4-hydroxybenzyl phosphonate, diethyl 3,5-di-tert-butyl-4-hydroxybenzylphosphonate, dioctadecyl 3,5-di-tert-butyl-4-hydroxybenzylphosphonate, dioctadecyl 5-tert-butyl-4-hydroxy-3-methylbenzylphosphonate, calcium salt of monoethyl 3,5-di-tert-butyl-4-hydroxybenzylphosphonate.

1.11. Acylaminophenols, for example 4-hydroxylauranilide, 4-hydroxystearanilide, octyl N-(3,5-di-tert-butyl-4-hydroxyphenyl)carbamate.

1.12. Esters of β-(3,5-di-tert-butyl-4-hydroxyphenyl)-propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxalamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.13. Esters of β-(5-tert-butyl-4-hydroxy-3-methylphenyl)propionic acid with mono- or polyhydric alcohols, e.g. methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(3,5-dicyclohexyl-4-hydroxyphenyl)propionic acid with mono- or polyhydric alcohols, e.g. methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of 3,5-di-tert-butyl-4-hydroxyphenylacetic acid with mono- or polyhydric alcohols, e.g. methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Amides of β-(3,5-di-tert-butyl-4-hydroxyphenyl)propionic acid, for example N,N'-bis(3,5-di-tert-butyl-4-hydroxyphenylpropionyl)hexamethylenediamine, N,N'-bis(3,5-di-tert-butyl-4-hydroxyphenylpropionyl)trimethylenediamine, N,N'-bis(3,5-di-tert-butyl-4-hydroxyphenylpropionyl)hydrazine.

2. UV absorbers and light stabilisers 2.1. 2-(2'-Hydroxyphenyl)benzotriazoles, for example the 5'-methyl, 3',5'-di-tert-butyl, 5'-tert-butyl, 5'-(1,1,3,3-tetramethylbutyl), 5-chloro-3',5'-di-tert-butyl, 5-chloro-3'-tert-butyl-5'-methyl, 3'-sec-butyl-5'-tert-butyl, 4'-octoxy, 3',5'-di-tert-amyl and 3',5'-bis(α,α-dimethylbenzyl) derivative, mixture of 5-chloro-3'-tert-butyl-5'-(2-octyloxycarbonylethyl)- and 5-chloro-3'-tert-butyl-5'-[2-(2-ethylhexyloxy)carbonylethyl]-, 5-chloro-3'-tert-butyl-5'-(2-methoxycarbonylethyl)-, 3'-tert-butyl-5'-(2-methoxycarbonylethyl)-, 3'-tert-butyl-5'-(2-octyloxycarbonylethyl)-, 3'-tert-butyl-5'-[2-(2-ethylhexyloxy)carbonylethyl]-, 3'-dodecyl-5'-methyl- and 3'-tert-butyl-5'-(2-isooctyloxycarbonylethyl)-2'-hydroxyphenyl-2H-2-benzotriazole, 2,2'-methylenebis[4-(1,1,3,3-tetramethylbutyl)-6-benzotriazol-2-ylphenol]; transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO(CH$_2$)$_3$]$_2$— where R is 3'-tert-butyl-4'-hydroxy-5'-2H-benzotriazol-2-ylphenyl.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivative.

2.3. Esters of substituted or unsubstituted benzoic acids, for example 4-tert-butylphenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate and hexadecyl 3,5-di-tert-butyl-4-hydroxybenzoate, octadecyl 3,5-di-tert-butyl-4-hydroxybenzoate and 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thiobis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of 4-hydroxy-3,5-di-tert-butylbenzylphosphonic acid monoalkyl esters, such as of the methyl or ethyl ester, nickel complexes of ketoximes, such as of 2-hydroxy-4-methylphenyl undecyl ketoxime, nickel complexes of 1-phenyl-4-lauroyl-5-hydroxypyrazole, with or without additional ligands.

2.6. Sterically hindered amines, for example bis(2,2,6,6-tetramethylpiperidyl) sebacate, bis(2,2,6,6-tetramethylpiperidyl) succinate, bis(1,2,2,6,6-pentamethylpiperidyl) sebacate, bis(1,2,2,6,6-pentamethylpiperidyl) n-butyl-3,5-di-tert-butyl-4-hydroxybenzylmalonate, the condensation product of 1-hydroxyethyl-2,2,6,6-tetramethyl-4-hydroxypiperidine and succinic acid, the condensation product of N,N'-bis(2,2,6,6-tetramethyl-4-piperidyl)hexamethylenediamine and 4-tert-octylamino-2,6-dichloro-1,3,5-s-triazine, tris(2,2,6,6-tetramethyl-4-piperidyl) nitrilotriacetate, tetrakis(2,2,6,6-tetramethyl-4-piperidyl) 1,2,3,4-butanetetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl) 2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperidyl) sebacate, bis(1-octyloxy-2,2,6,6-tetramethylpiperidyl) succinate, condensation product of N,N'-bis(2,2,6,6-tetramethyl-4-piperidyl)hexamethylenediamine and 4-morpholino-2,6-dichloro-1,3,5-triazine, condensation product of 2-chloro-4,6-di(4-n-butylamino-2,2,6,6-tetramethylpiperidyl)-1,3,5-triazine and 1,2-bis(3-aminopropylamino(ethane, condensation product of 2-chloro-4,6-di(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)pyrrolidine-2,5-dione.

2.7. Oxamides, for example 4,4'-dioctyloxyoxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylaminopropyl)oxamide, 2-ethoxy-5-tert-butyl-2'-ethyloxanilide and its mixture with 2-ethoxy-2'-ethyl-5,4'-di-tert-butyloxanilide and mixtures of o- and p-methoxy-disubstituted oxanilides, and o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2- hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2-hydroxy-3-butyloxypropyloxy)phenyl]-4,6-bis(2,4-dimethylphenyl)-1,3,5-triazine, 2-[2-hydroxy-4-(2-hydroxy-3-octyloxypropyloxy) phenyl]-4,6-bis(2,4-dimethylphenyl)-1,3,5-triazine.

3. Metal deactivators, for example N,N'-diphenyloxamide N-salicylal-N'-salicyloylhydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalic dihydrazide, oxanilide, isophthalic dihydrazide, sebacic diphenylhydrazide, adipic N,N'-diacetyl dihydrazide, oxalic N,N'-bis(salicyloyl) dihydrazide, thiodipropionic N,N'-bis(salicyloyl)dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl) pentaerythritol diphosphite, bis(isodecyloxy) pentaerythritol diphosphite, bis(2,4-di-tert-butyl-6-methylphenyl) pentaerythritol diphosphite, bis(2,4,6-tri-tert-butylphenyl) pentaerythritol diphosphite, tristearyl sorbitol triphosphite, tetrakis(2,4-di-tert-butylphenyl) 4,4'-biphenylenediphosphonite, 6-isooctyloxy-2,4,8,10-tetra-tert-butyl-12H-dibenz[d,g]-1,3,2-dioxaphosphocin, 6-fluoro-2,4,8,10-tetra-tert-butyl-12-methyl-dibenz[d,g]-1,3,2-dioxaphosphocin.

5. Compounds which destroy peroxides, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilisers, for example copper salts in combination with iodides and/or phosphorus compounds and salts of divalent manganese.

7. Basic co-stabilisers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate, potassium palmitate, antimony pyrocatecholate or tin pyrocatecholate.

8. Nucleating agents, for example 4-tert-butyl-benzoic acid, adipic acid, diphenylacetic acid.

9. Fillers and reinforcing agents, for example calcium carbonate, silicates, glass fibres, asbestos, talc, kaolin, mica, barium sulfate, metal oxides and hydroxides, carbon black, graphite.

10. Other additives, for example plasticisers, lubricants, emulsifiers, pigments, fluorescent whitening agents, flameproofing agents, antistatic agents and blowing agents.

If the compositions according to the invention are those based on lubricants and hydraulic fluids, they can also contain other additives which are added to improve certain use properties, for example other antioxidants, metal deactivators, rust inhibitors, viscosity index improvers, pour point reducers, dispersants/surfactants and abrasion resistance additives.

Examples of antioxidants are to be taken from the listing reproduced above under the title "1. Antioxidants", in particular items 1.1 to 1.10. Examples of other additional additives are the following:

Examples of amine antioxidants: N,N'-di-isopropyl-p-phenylenediamine, N,N'-di-sec-butyl-p-phenylenediamine, N,N'-bis(1,4-dimethyl-pentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-di-(naphthyl-2)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfonamido)-diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-phenyl-2-naphthylamine, octylated diphenylamine, such as p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, di-(4-methoxyphenyl)-amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-di-[(2-methylphenyl)-amino]-ethane, 1,2-di-(phenylamino)-propane, (o-tolyl)-biguanide, di-[4-(1',3'-dimethylbutyl)-phenyl]amine, tert-octylated N-phenyl-1-naphthylamine, mixture of mono- and dialkylated tert-butyl/tert-octyldiphenylamines, 2,3-dihydro-3,3-dimethyl-4H-1,4-benzothiazine, phenothiazine, N-allylphenothiazine.

Examples of other antioxidants: aliphatic or aromatic phosphites, esters of thiodipropionic acid or thiodiacetic acid, or salts of dithiocarbamic or dithiophosphoric acid.

Examples of metal deactivators, for example for copper, are: triazoles, benzotriazoles and derivatives thereof, tolutriazoles and derivatives thereof, 2-mercaptobenzothiazole, 2-mercaptobenzotriazole, 2,5-dimercaptobenzotriazole, 2,5-dimercaptobenzothiadiazole, 5,5'-methylenebisbenzotriazole, 4,5,6,7-tetrahydrobenzotriazole, salicylidenepropylenediamine, salicylaminoguanidine and salts thereof.

Examples of rust inhibitors are: a) Organic acids, their esters, metal salts and anhydrides, for example: N-oleoylsarcosine, sorbitan monooleate, lead naphthenate, alkenylsuccinic anhydride, for example dodecenylsuccinic anhydride, alkenylsuccinic acid partial esters and partial amides, 4-nonylphenoxyacetic acid.

b) Nitrogen-containing compounds, for example: I. Primary, secondary or tertiary aliphatic or cycloaliphatic amines and amine salts of organic and inorganic acids, for example oil-soluble alkylammonium carboxylates. II. Heterocyclic compounds, for example: substituted imidazolines and oxazolines. c) Phosphorus-containing compounds, for example: amine salts of phosphoric acid partial esters or phosphonic acid partial esters, zinc dialkyldithiophosphates. d) Sulfur-containing compounds, for example: barium dinonylnaphthalenesulfonates, calcium petroleumsulfonates.

Examples of viscosity index improvers are: polyacrylates, polymethacrylates, vinylpyrrolidone/methacrylate copolymers, polyvinylpyrrolidones, polybutenes, olefin copolymers, styrene/acrylate copolymers, polyethers.

Examples of pour point reducers are: polymethacrylate, alkylated naphthalene derivatives.

Examples of dispersants/surfactants are: polybutenylsuccinamides or -imides, polybutenylphosphonic acid derivatives, basic magnesium sulfonates and phenolates, calcium sulfonates and phenolates, and barium sulfonates and phenolates.

Examples of abrasion resistance additives are: sulfur-and/or phosphorus-and/or halogen-containing compounds, such as sulfurised vegetable oils, zinc dialkyldithiophosphates, tritolyl phosphate, chlorinated paraffins, alkyl and aryl di- and trisulfides, triphenyl phosphorothionates, diethanolaminomethyltolytriazole, di(2-ethylhexyl)aminomethyltolyltriazole.

The sulfoxides of the present invention of the formula I or II can be obtained, for example, by oxidation of compounds of the formula III. Examples of suitable oxidising agents are hydrogen peroxide or percarboxylic acids, organic hydroperoxides or other suitable organic or inorganic oxidising agents, it being possible for the reactions to be carried out by methods known from the relevant literature. Examples of suitable percarboxylic acids are m-chloroperbenzoic acid, peracetic acid or trifluoroperacetic acid. Examples of hydroperoxides which can be used are tert-butyl hydroperoxide and cumene hydroperoxide.

The starting materials can also be oxidised with oxidising agents prepared in situ. Examples of oxidising agents of this type are percarboxylic acids which are formed in a mixture of hydrogen peroxide and carboxylic acids.

Depending on the product desired, the oxidising agent is advantageously added in a stoichiometric amount or in excess. The reaction parameters are selected such that further oxidation of the sulfoxides to sulfones is minimal. The oxidation is advantageously carried out in the presence of solvents. Examples of the solvents used are non-oxidisable organic solvents, for example chlorinated hydrocarbons, ketones or hydrocarbons. Examples of suitable chlorinated hydrocarbons are methylene chloride or chloroform, examples of suitable ketones are acetone, methyl ethyl ketone or methyl isopropyl ketone, and suitable hydrocarbons are in particular aromatic hydrocarbons, for example toluene or xylene.

The reaction temperature can be, for example, between −40° and +80° C. Depending on the temperature and the specific reaction, the reaction times are, for example, between 10 minutes and 24 hours.

The starting materials, the compounds of the formula III and their preparation are known from the literature and are described in a large number of patents, for example U.S. Pat. No. 4,759,862 and U.S. Pat. No. 4,857,572 and can be prepared analogously to the processes described there.

The mixtures according to the invention can be prepared from the compounds of the formula I or II and those of the formula III, for example, by mixing the individual compounds in the desired relative amounts. However, it is preferred to obtain these mixtures by partial oxidation of compounds of the formula III, for example by the abovementioned methods, the oxidising agent being used in a less than stoichiometric amount. Its amount depends on the desired content of the compound of the formula I or II or III in the mixture. It can be easily determined by simple preliminary tests or calculation.

More detailed information is available from the preparation examples which follow.

The examples which follow illustrate the invention further. Parts or percentages given in the remaining description as well as in the patent claims are by weight, unless stated otherwise.

EXAMPLE 1

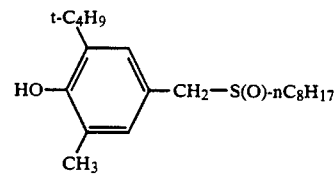

5.7 g of 30% hydrogen peroxide are added dropwise at 0° C. to 16.1 g (0.05 mol) of 2-tert-butyl-6-methyl-4-(n-octylthiomethyl)phenol, dissolved in 120 ml of acetone. After stirring at room temperature for 26 hours, the solvent is distilled off under reduced pressure. Chromatography on silica gel using methylene chloride/ethyl acetate in a ratio of 9:1 as eluent gives 12.2 g of 2-tert-butyl-6-methyl-4-(octylsulfinylmethyl)phenol as a yellowish oil.

| Elemental analysis: | calculated: | C 70.96% | found: | C 70.98% |
|---|---|---|---|---|
| | | H 10.12% | | H 9.89% |
| | | S 9.47% | | S 9.40% |

EXAMPLES 2–14

0.05 mol of the particular substituted thiomethylphenol of the formula III are dissolved, depending on the solubility of educt and product, in acetone or methylene chloride. 0.05 mol of 30% hydrogen peroxide are added dropwise at 0°–20° C. over a period of 5–10 minutes. The mixture is then stirred at room temperature for 4–20 hours. The reaction is checked for completion by thin-layer chromatography. The solvent is then distilled off under reduced pressure. The products are obtained in pure form by chromatography on silica gel, using an eluent. The products of Examples 2–14 are listed in

TABLE 1

The characteristic $^1$H nuclear magnetic resonance data are reproduced in Table 2.

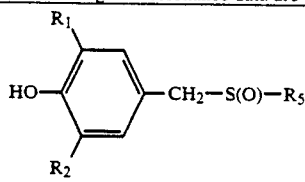

| Example No. | $R_1$ | $R_2$ | $R_5$ | Melting point [°C.] | Eluent |
|---|---|---|---|---|---|
| 1 | Methyl | t-Butyl | n-$C_8H_{17}$ | Oil | C |
| 2 | Methyl | t-Butyl | n-$C_{12}H_{25}$ | Oil | C |
| 3 | Methyl | Methyl | n-$C_8H_{17}$ | 104 | D |
| 4 | Methyl | Cyclopent-3-enyl | n-$C_8H_{17}$ | Oil | (c) |
| 5 | Methyl | Cyclopent-3-enyl | n-$C_{12}H_{25}$ | 74 | A |
| 6 (a) | t-Butyl | t-Butyl | $CH_2COOC_8H_{17}$* | Oil | B |
| 7 | t-Butyl | t-Butyl | $CH_2COOC_{13}H_{27}$* | Oil | E |
| 8 | t-Butyl | t-Butyl | $CH_2COOC_{18}H_{37}$* | 62 | B |
| 9 | Methyl | Cyclopent-3-enyl | $CH_2COOC_8H_{17}$* | Oil | A |
| 10 | t-Butyl | t-Butyl | $CH_2COO$-EH** | Oil | F |
| 11 (b) | t-Butyl | t-Butyl | $CH(CH_3)COO$-EH** | Oil | F |
| 12 (b) | Methyl | t-Butyl | $CH(CH_3)COO$-EH** | Oil | F |
| 13 (b) | t-Butyl | t-Butyl | Phenyl | 124 | F |
| 14 (b) | Methyl | t-Butyl | Phenyl | Resin | F |

*Mixture of isomers
**2-Ethylhexyl
(a) Use of 0.1 mol of hydrogen peroxide
(b) Solvent acetic acid (work-up: first washing with sodium bicarbonate solution)
(c) The product is obtained pure without chromatography
Eluent:
A Methylene chloride/ethyl acetate (49:1)
B Methylene chloride/ethyl acetate (19:1)
C Methylene chloride/ethyl acetate (9:1)
D Hexane/methylene chloride/ethyl acetate (6:4:1)
E Methylene chloride
F Hexane/ethyl acetate (7:1)

TABLE 2

Characteristic $^1$H NMR signals of the compounds of Examples 2-14, measured in deuterochloroform at 100 MHz (standard tetramethylsilane)

| | ArylCH$_2$—SO | | SOCH$_2$COO | |
|---|---|---|---|---|
| Example No. | δ [ppm] | $J_{AB}$ [Hz] | δ [ppm] | $J_{AB}$ [Hz] |
| 1 | 3.96/3.80 | 13 | | |
| 2 | 3.96/3.80 | 13.5 | | |
| 3 | 3.92/3.77 | 13.5 | | |
| 4 | 3.95/3.78 | 14 | | |
| 5 | 3.96/3.77 | 13 | | |
| 6 | 4.19/4.02 | 13.5 | 3.64/3.49 | 13.5 |
| 7 | 4.16/4.04 | 12.5 | 3.61/3.51 | 12.5 |
| 8 | 4.15/4.04 | 12.5 | 3.61/3.51 | 12.5 |
| 9(*) | 4.14/3.97 | 13.5 | 3.64/3.48 | 13.5 |
| 10(**) | 4.19/4.02 | 13 | 3.64/3.51 | 12 |
| 11 | 4.05/3.88 | 13 | (***) | — |
| 12 | 4.04/3.89 | 12.5 | (****) | — |
| 13 | 4.13/3.85 | 12.5 | | |
| 14 | 4.07/3.86 | 12.5 | | |

*at 300 MHz, **at 250 MHz
***3 quartets ($^3J_{HH}$ = 7) at 3.69/3.47 and 3.35 (CHCH$_3$) mixture of diastereomers
****3 quartets ($^3J_{HH}$ = 7) at 3.70/3.48 and 3.35 (CHCH$_3$) mixture of diastereomers

EXAMPLE 15

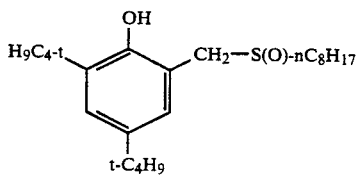

The procedure described in Example 1 is repeated, 18.2 g of 2,4-bis(tert-butyl)-6-octylthiomethylphenol being reacted with an equimolar amount of hydrogen peroxide, to give, after column chromatography using hexane/ethyl acetate (9:1), 11.95 g of 2,4-bis(tert-butyl)-6-octylsulfinylmethylphenol of melting point 58°–59° C.

| Elemental analysis: | calculated: | C 72.58% | found: | C 72.58% |
|---|---|---|---|---|
| | | H 10.59% | | H 10.29% |
| | | S 8.42% | | S 8.49% |

Characteristic $^1$H nuclear magnetic resonance signals: 4.31 and 3.86 ppm ($J_{AB}$=14 Hz).

EXAMPLE 16

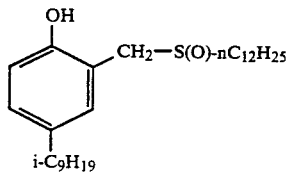

Analogously to the procedure described in Example 1, 8.17 g of 2-dodecylthiomethyl-4-nonylphenol, which is obtained by alkylthiomethylation of technical grade 4-nonylphenol (mixture of isomers) with formaldehyde and 1-dodecanethiol, are reacted with hydrogen peroxide solution. After column chromatography using hexane/ethyl acetate (4:1), 6.7 g of 2-dodecylsulfinylmethyl-4-nonylphenol are isolated as a colourless oil.

| Elemental analysis: | calculated: | C 74.61% | found: | C 74.67% |
|---|---|---|---|---|
| | | H 11.18% | | H 11.10% |

S 7.11%    S 7.14%

Characteristic ¹H nuclear magnetic resonance signals: ~4.45 and ~3.80 ppm ($J_{AB}=14$ Hz)

EXAMPLES 17-18

The compounds are prepared analogously to the method described in Example 1. They are listed in Table 3, while the characteristic nuclear magnetic resonance signals of the corresponding compounds are listed in Table 4.

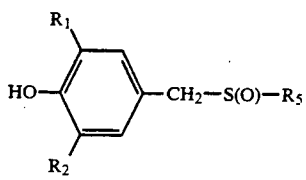

TABLE 3

| Example No. | $R_1$ | $R_2$ | $R_5$ | Melting point [°C.] | Work-up |
|---|---|---|---|---|---|
| 17 | t-Octyl* | Methyl | Phenyl | Oil | Chromatography on silica gel Eluent hexane/ethyl acetate (5:1) |
| 18 | t-Octyl* | Methyl | Benzyl | 143 | recrystallised from cyclohexane |

*1,1,3,3-Tetramethylbutyl

EXAMPLE 19

Example 6 is repeated, using only 1.1 equivalents of hydrogen peroxide instead of a two-fold excess, to give, after evaporation of the reaction mixture without further separation, an orange resin which according to ¹H NMR constitutes a mixture of the starting thioether and the sulfoxide in a ratio of 1:2.

EXAMPLE 20

Example 6 is repeated, using 0.5 equivalent of hydrogen peroxide instead of a two-fold excess, to give, after evaporation of the reaction mixture without further separation, an orange viscous oil which according to ¹H NMR constitutes a mixture of the starting thioether and the sulfoxide in a ratio of 2:1.

EXAMPLES 21-40

The compounds of Examples 21-40 are prepared analogously to the compounds of Examples 2-14. The compounds are listed in Tables 5a and 5b, while the characteristic ¹H nuclear magnetic resonance data can be seen from Table 6. The chemical shift values ($\delta$) are listed in [ppm] relative to tetramethylsilane. Deuterochloroform was used as the solvent.

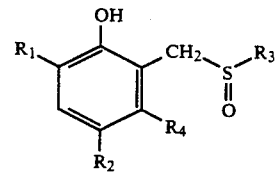

TABLE 5a

For all compounds of this table, $R_4$ is hydrogen

| Ex. No. | $R_1$ | $R_2$ | $R_3$ | Melting point [°C.] | Eluent |
|---|---|---|---|---|---|
| 21 | 2-$C_{18}H_{37}$[1) | Methyl | $C_{12}H_{25}$ | yellowish liquid | F |
| 22 | 2-$C_{18}H_{37}$[1) | Methyl | t-$C_{12}H_{25}$[3) | yellowish oil | B |
| 23 | 2-$C_{18}H_{37}$[1) | Methyl | $C_8H_{17}$ | yellowish oil | B |
| 24 | 2-$C_{18}H_{37}$[1) | Methyl | t-$C_8H_{17}$[4) | colourless oil | B |
| 25 | t-$C_8H_{17}$[2) | Methyl | $C_{12}H_{25}$ | yellowish oil | D*) |
| 26 | t-$C_8H_{17}$[2) | Methyl | $C_8H_{17}$ | yellowish viscous oil | B*) |
| 27 | t-$C_8H_{17}$[2) | Methyl | $CH_2COO^iC_8H_{17}$[5) | yellow oil | E |
| 28 | t-$C_8H_{17}$[2) | Methyl | $CH_2COO^iC_{13}H_{27}$[6) | yellowish oil | E |
| 29 | t-Butyl | t-Butyl | $C_{12}H_{25}$ | yellow oil | B |
| 30 | t-Butyl | t-Butyl | t-$C_{12}H_{25}$[3) | yellowish resin | B |
| 31 | t-Butyl | t-Butyl | 2-$C_8H_{17}$[7) | yellowish resin | B |
| 32 | t-Butyl | t-Butyl | t-$C_9H_{19}$[7) | orange resin | B |
| 33 | t-Butyl | t-Butyl | $CH_2COO^iC_8H_{17}$[5) | yellow oil | C |
| 34 | t-Butyl | t-Butyl | $CH_2COO^iC_{13}H_{27}$[6) | yellowish resin | A |
| 35 | Methyl | Methyl | $C_{12}H_{25}$ | yellowish liquid | B |
| 36 | Methyl | Methyl | t-$C_{12}H_{25}$[3) | yellowish resin | B |
| 37 | Methyl | Methyl | t-$C_9H_{19}$[7) | yellowish viscous oil | A |
| 38 | Methyl | Methyl | $CH_2COO^iC_{13}H_{27}$[6) | yellow oil | B |

TABLE 4

Characteristic ¹H NMR signals of the compounds of Examples 17-18, measured in deuterochloroform at 100 MHz (standard tetramethylsilane)

| | ArylCH₂SO | | PhenylCH₂SO | |
|---|---|---|---|---|
| Example No. | $\delta$ [ppm] | $J_{AB}$ [Hz] | $\delta$ [ppm] | $J_{AB}$ [Hz] |
| 17 | 4.29/3.95 | 13.5 | — | — |
| 18 | 4.27/3.82 | 14 | 4.00/3.84 | 13 |

TABLE 5b

| Ex. No. | $R_1$ | $R_2$ | $R_3$ | $R_4$ | Melting point [°C.] | Eluent |
|---|---|---|---|---|---|---|
| 39 | t-Butyl | t-Butyl | t-$C_9H_{19}$ | Methyl | orange resin | B |

TABLE 5b-continued

| Ex. No. | $R_1$ | $R_2$ | $R_3$ | $R_4$ | Melting point [°C.] | Eluent |
|---|---|---|---|---|---|---|
| 40 | t-Butyl | t-Butyl | $CH_2CH_2OH$ | Methyl | 163 | G**) |

A Hexane/ethyl acetate 49:1
B Hexane/ethyl acetate 9:1
C Hexane/acetone 8:1
D Hexane/methylene chloride 1:1
E Hexane/acetone 9:1
F Hexane/ethyl acetate 4:1
G Hexane/ethyl acetate 7:3
1) 2-$C_{18}H_{37}$:n-octadecan-2-yl
2) t-$C_8H_{17}$:1,1,3,3-tetramethylbutyl
3) t-$C_{12}H_{25}$:mixture of isomers comprising 1,1,3,3,5,5-hexamethylhexyl and 2,2,4,6,6-pentamethylhept-4-yl
4) $CH_2COOC_8H_{17}$:ester of primary octanol-mixture of isomers
5) Mixture of isomers
6) 2-$C_8H_{17}$:n-octan-2-yl
7) t-$C_9H_{19}$:mixture of isomers
*) Additional purification by column chromatography
**) Recrystallised from acetone

TABLE 6

| Ex. No. | $ArCH_2SO$ δ [ppm] | Coupling constant [Hz] of the AB system |
|---|---|---|
| 21 | 4.35 4.32 3.80 3.77 | 14 |
| 22 | 4.40–4.20 (m) and 3.4–3.55 (m) a) | |
| 23 | 4.35 4.32 3.82 3.79 | 14 |
| 24 | 4.24 3.49 3.48 b) | 13 |
| 25 | 4.34 3.76 | 14 |
| 26 | 4.35 3.76 | 14 |
| 27 | 4.59 3.97 | 14 |
| 28 | 4.60 3.97 | 14 |
| 29 | 4.30 3.92 | 14 |
| 30 | 4.3–4.45 (m) and 3.35–3.55 (m) b) | |
| 31 | 3.9–4.3 (m) b) | |
| 32 | 4.2–4.45 (m) and 3.35–3.55 (m) b) | |
| 33 | 4.59 4.08 | 14 |
| 34 | 4.60 4.08 | 14 |
| 35 | 4.35 3.50 | 14 |
| 36 | 4.15–4.35 (m) and 3.4–3.6 (m) b) | |
| 37 | 4.15–4.40 (m) and 3.4–3.55 (m) b) | |
| 38 | 4.56 4.01 | 14 |
| 39 | 4.3–4.4 (m) and 3.65–3.72 (m) b) | |
| 40 | 4.50 4.16 | 14 | a) Mixture of diastereomers
b) Mixture of isomers
(m) Multiplet

EXAMPLE 41

Stabilisation of Polybutadiene Rubber (Brabender Test)

100 parts of polybutadiene prestabilised with 0.36% of 2,6-di-tert-butyl-p-cresol are kneaded in a Brabender plastograph together with 0.25% of the stabiliser to be tested at 160° C. and 60 rpm for 30 minutes.

The apparatus operates by the following principle:

The kneading rolls rotating in a heated kneading chamber controlled by a thermostat are driven by a motor supported in pendulum manner. To overcome the flow resistance of the plastic in the kneading chamber, a certain torque is necessary which is displayed by means of the torque pendulum and recorded as a function of time. From the torque curve, the induction time, i.e. the kneading time in minutes until the torque increases by 100 mp, following the torque minimum, is determined. The tests show that the added stabiliser keeps the flow resistance constant for a substantially longer period of time, i.e. the plastic is stable for a longer period of time. The results are listed in Table 5.

TABLE 5

| Compound from Example No. | Brabender induction time [min] |
|---|---|
| blank* | 9.5 |
| 1 | >30 |
| 3 | >30 |
| 6 | >30 |
| 7 | >30 |
| 8 | >30 |
| 9 | >30 |
| 10 | >30 |

*the blank does not contain a stabiliser according to the invention

What is claimed is:

1. A compound of the formula I

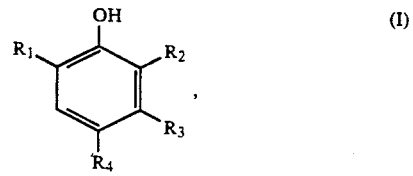

in which $R_1$ is hydrogen, $C_1$–$C_{20}$alkyl, $C_2$–$C_{18}$alkenyl, $C_5$–$C_7$cycloalkyl, $C_5$–$C_7$cycloalkenyl, phenyl or $C_7$–$C_9$phenylalkyl, $R_2$ is hydrogen, $C_1$–$C_{20}$alkyl, $C_2$–$C_{18}$alkenyl, $C_5$–$C_7$cycloalkyl, $C_5$–$C_7$cycloalkenyl, phenyl, $C_7$–$C_9$phenylalkyl or a radical —$CH_2$—SO—$R_5$, in which $R_5$ is $C_8$–$C_{20}$alkyl which may be interrupted by —O—, —S— or —SO— groups, mono- or dihydroxy-substituted $C_2$–$C_{12}$alkyl, phenyl, benzyl, —($CH_2$)$_n$COOR$_6$ or —$CH(CH_3)COOR_6$, in which $R_6$ is $C_1$–$C_{20}$alkyl and n is 1 or 2, $R_3$ is hydrogen or a group —$CH_2$—SO—$R_5$, in which $R_5$ is as defined above, and $R_4$ has the same meanings as $R_2$, with the proviso that one of the radicals $R_2$, $R_3$ or $R_4$ is the group —$CH_2$—SO—$R_5$ and that, if $R_4$ is —$CH_2$—SO—$R_5$ and $R_1$ and $R_2$ are simultaneously tert-butyl or tert-amyl, $R_5$ is not $C_8$–$C_{14}$alkyl.

2. A compound according to claim 1, in which $R_1$ is hydrogen, $C_1$–$C_{18}$alkyl, $C_5$–$C_6$cycloalkyl or $C_5$–$C_7$cycloalkenyl, $R_2$ has the same definition as $R_1$ or is —$CH_2$—SO—$R_5$, $R_3$ is hydrogen, $R_4$ is hydrogen, $C_1$–$C_{18}$alkyl or —$CH_2$—SO—$R_5$, $R_5$ is $C_8$–$C_{20}$alkyl, phenyl, benzyl or —$CH_2COOR_6$ and $R_6$ is $C_1$–$C_{20}$alkyl.

3. A compound according to claim 1, in which $R_1$ is $C_1$–$C_{18}$alkyl, $R_2$ is $C_1$–$C_{12}$alkyl, cyclopentenyl or —$CH_2$—SO—$R_5$, $R_3$ is hydrogen, $R_4$ is $C_1$–$C_{12}$alkyl or —$CH_2$—SO—$R_5$, $R_5$ is $C_8$–$C_{20}$alkyl, phenyl, benzyl, —$CH(CH_3)COOR_6$, —$CH_2CH_2OH$ or —$CH_2COOR_6$ and $R_6$ is $C_6$–$C_{20}$alkyl.

4. A compound according to claim 1, in which $R_1$ is hydrogen, $C_1$–$C_{18}$alkyl, $C_5$–$C_6$cycloalkyl or $C_5$–$C_6$cycloalkenyl, $R_2$ is —$CH_2$—SO—$R_5$, $R_3$ is hydrogen, $R_4$ is $C_1$–$C_{18}$alkyl, $C_5$–$C_6$cycloalkyl or $C_5$–$C_6$cycloalkenyl, and $R_5$ is $C_8$–$C_{20}$alkyl, phenyl, benzyl or —$CH_2COOR_6$.

5. A compound according to claim 4, in which $R_1$ is hydrogen, $C_1$–$C_{12}$alkyl or $C_5$–$C_6$cycloalkyl and $R_5$ is $C_8$–$C_{18}$alkyl, phenyl, benzyl or —$CH_2COOR_6$.

6. A compound according to claim 5, in which $R_1$ is $C_1$–$C_9$alkyl and $R_5$ is $C_8$–$C_{12}$alkyl, phenyl or benzyl.

7. A compound according to claim 6, in which $R_5$ is $C_8$–$C_{12}$alkyl.

8. A compound according to claim 1, in which $R_1$ and $R_2$, independently of one another, are $C_1$–$C_{18}$alkyl, $C_5$–$C_6$cycloalkyl or $C_5$–$C_6$cycloalkenyl, $R_3$ is hydrogen and $R_4$ is a radical —$CH_2$—SO—$R_5$, in which $R_5$ is $C_8$–$C_{18}$alkyl, phenyl, benzyl, —$CH_2CH_2OH$ or —$(CH_2)_nCOOR_6$.

9. A compound according to claim 8, in which $R_5$ is —$(CH_2)_nCOOR_6$.

10. A compound according to claim 8, in which $R_1$ and $R_2$, independently of one another, are $C_1$–$C_{12}$alkyl, $C_5$–$C_6$cycloalkyl or $C_5$–$C_6$cycloalkenyl and $R_5$ is $C_8$–$C_{18}$alkyl, phenyl, benzyl or —$(CH_2)_nCOOR_6$.

11. A compound according to claim 10, in which $R_1$ is $C_1$–$C_9$alkyl and $R_5$ is $C_8$–$C_{12}$alkyl, phenyl or benzyl.

12. A compound according to claim 11, in which $R_5$ is $C_8$–$C_{12}$alkyl.

13. A mixture of at least one of the compounds defined in claim 1 with at least one compound of the formula III

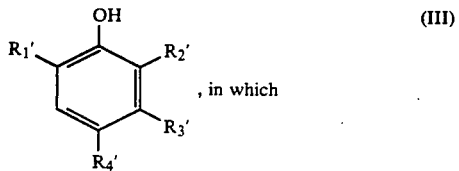

, in which $R_1'$ is hydrogen, $C_1$–$C_{20}$alkyl, $C_2$–$C_{18}$alkenyl, $C_5$–$C_7$cycloalkyl, $C_5$–$C_7$cycloalkenyl, phenyl or $C_7$–$C_9$phenylalkyl, $R_2'$ is hydrogen, $C_1$–$C_{20}$alkyl, $C_2$–$C_{18}$alkenyl, $C_5$–$C_7$cycloalkyl, $C_5$–$C_7$cycloalkenyl, phenyl, $C_7$–$C_9$phenylalkyl or a radical —$CH_2$—S—$R_5$, in which $R_5$ is $C_8$–$C_{20}$alkyl which may be interrupted by —O—, —S— or —SO— groups, mono- or dihydroxy-substituted $C_2$–$C_{12}$alkyl, phenyl, benzyl, —$(CH_2)_nCOOR_6$ or —$CH(CH_3)COOR_6$, in which $R_6$ is $C_1$–$C_{20}$alkyl and n is 1 or 2, $R_3'$ is hydrogen or a group —$CH_2$—S—$R_5$, in which $R_5$ is as defined above, and $R_4'$ has the same meanings as $R_2'$, with the proviso that one of the radicals $R_2'$, $R_3'$ or $R_4'$ is the group —$CH_2$—S—$R_5$.

14. A mixture according to claim 13, in which the components of the formula I or II differ from those of the formula III only by the latter containing —S— groups instead of —SO— groupings but otherwise have the same structure as the former.

15. A mixture according to claim 13 or 14, obtainable by partial oxidation of at least one compound of the formula III.

16. A mixture according to claim 13 or 14, in which the ratio of the compounds of the formula III to those of the formula I or II is 1:9 to 9:1.

17. A mixture according to claim 16, in which the ratio of the compounds of the formula III to those of the formula I or II is 1:9 to 1:1.

18. A composition comprising an organic material which is sensitive to oxidative, thermal and/or light-induced degradation and at least one compound of the formula I according to claim 1 or at least one mixture defined in claim 13.

19. A composition according to claim 18 comprising at least one compound of the formula I.

20. A composition according to claim 18, in which the organic material is an organic polymer, a lubricant or a hydraulic fluid.

21. A composition according to claim 18, in which the organic material is an elastomer or a lubricant.

22. A process for stabilising a material which is sensitive to oxidative, thermal and/or light-induced degradation, which comprises incorporating at least one compound of the formula I according to claim 1 or a mixture according to claim 13 in this material or applying it thereto.

* * * * *